(12) United States Patent
Cho et al.

(10) Patent No.: US 9,532,767 B2
(45) Date of Patent: Jan. 3, 2017

(54) ULTRASONIC PROBE APPARATUS AND METHOD OF MANUFACTURING ULTRASONIC PROBE APPARATUS

(71) Applicant: SAMSUNG ELECTRONICS CO., LTD., Suwon-si (KR)

(72) Inventors: Kyung Il Cho, Seoul (KR); Dong Wook Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 320 days.

(21) Appl. No.: 13/870,285

(22) Filed: Apr. 25, 2013

(65) Prior Publication Data

US 2013/0289410 A1 Oct. 31, 2013

(30) Foreign Application Priority Data

Apr. 25, 2012 (KR) .......................... 10-2012-0043354

(51) Int. Cl.
| | |
|---|---|
| *A61B 8/14* | (2006.01) |
| *A61B 8/00* | (2006.01) |
| *G01S 15/89* | (2006.01) |
| *B06B 1/06* | (2006.01) |

(52) U.S. Cl.
CPC ........... *A61B 8/4444* (2013.01); *A61B 8/4494* (2013.01); *B06B 1/0622* (2013.01); *G01S 15/8913* (2013.01); *G01S 15/8925* (2013.01); *A61B 8/4477* (2013.01); *Y10T 29/49005* (2015.01)

(58) Field of Classification Search
None
See application file for complete search history.

(56) References Cited

U.S. PATENT DOCUMENTS

| | | | | |
|---|---|---|---|---|
| 5,797,845 | A * | 8/1998 | Barabash et al. | 600/443 |
| 6,443,901 | B1 * | 9/2002 | Fraser | 600/459 |
| 7,557,489 | B2 | 7/2009 | Petersen et al. | |
| 2010/0249605 | A1 | 9/2010 | Degertekin | |
| 2011/0071396 | A1 | 3/2011 | Sano et al. | |
| 2011/0071397 | A1 | 3/2011 | Wodnicki et al. | |
| 2011/0073968 | A1 * | 3/2011 | Ezaki et al. | 257/416 |

FOREIGN PATENT DOCUMENTS

| | | | | |
|---|---|---|---|---|
| EP | 0689187 | * | 12/1995 | G10K 11/32 |
| JP | 3325716 | B2 | 7/2002 | |
| JP | 4071084 | B2 | 1/2008 | |

(Continued)

OTHER PUBLICATIONS

Zhuang et al., "Integration of Trench-Isolated Through-Wafter Interconnects with 2D Capacitive Micromachined Ultrasonic Transducer Arrays." Sensors Actuatores A Phys., Jul. 20, 2007; 138(1); pp. 221-229.*

(Continued)

*Primary Examiner* — James Kish
(74) *Attorney, Agent, or Firm* — Sughrue Mion, PLLC

(57) ABSTRACT

An ultrasonic probe apparatus and a method of manufacturing the ultrasonic probe apparatus are provided. The ultrasonic probe apparatus may include at least one first tile which transmits an ultrasonic beam toward a target object, and at least one second tile which receives an ultrasonic beam which is reflected from the target object.

14 Claims, 7 Drawing Sheets

(56) References Cited

FOREIGN PATENT DOCUMENTS

| JP | 2008-518553 A | 5/2008 |
|---|---|---|
| JP | 2008289599 A | 12/2008 |
| JP | 2009-72370 A | 4/2009 |
| JP | 4370120 B2 | 9/2009 |
| JP | 4583901 B2 | 9/2010 |
| JP | 2011-505205 A | 2/2011 |
| KR | 10-2011-0088384 A | 8/2011 |
| KR | 10-2012-0000696 A | 1/2012 |

OTHER PUBLICATIONS

Communication dated Jul. 4, 2013 issued by the Korean Intellectual Property Office in counterpart Korean Patent Application No. 10-2012-0043354.

* cited by examiner

ULTRASONIC PROBE APPARATUS AND METHOD OF MANUFACTURING ULTRASONIC PROBE APPARATUS

CROSS-REFERENCE TO RELATED APPLICATION(S)

This application claims priority from Korean Patent Application No. 10-2012-0043354, filed on Apr. 25, 2012, in the Korean Intellectual Property Office, the disclosure of which is incorporated herein by reference in its entirety for all purposes.

BACKGROUND

1. Field

The following description relates to an ultrasonic probe apparatus which includes a send-only first tile which transmits an ultrasonic beam and a receive-only second tile which receives an ultrasonic beam.

2. Description of Related Art

A diagnostic ultrasound system is an apparatus that may radiate, from a surface of a target object or body, an ultrasonic beam toward a desired part inside the target object or body, and may obtain, for example, an image which relates to a cross section of soft tissues or an image of a blood flow, by using a reflected ultrasonic beam.

The diagnostic ultrasound system may include an ultrasonic probe apparatus that may obtain ultrasonic data by transmitting an ultrasonic beam toward the target object and receiving an ultrasonic beam which is reflected from the target object.

In particular, the ultrasonic probe apparatus may obtain imaging data relating to the target object by transmitting and receiving an ultrasonic beam while moving along with the target object, which remains in contact with the ultrasonic probe apparatus.

SUMMARY

In one general aspect, there is provided an ultrasonic probe apparatus, including n first tiles which transmit an ultrasonic beam toward a target object, and m second tiles, which are disposed along a virtual line that is provided in a predetermined form, and which receive an ultrasonic beam that is reflected from the target object. In particular, each of n and m denotes a natural number.

Each of the m second tiles includes a respective channel which is associated with the ultrasonic beam, and each of the m second tiles may be disposed such that each respective channel is disposed on the virtual line.

Each of the n first tiles and each of the m second tiles may be disposed such that each of a first gap among respective adjacent pairs of the n first tiles and a second gap among respective adjacent pairs of the m second tiles is maintained to be less than a predetermined value.

Each of the n first tiles and each of the m second tiles may include a respective Application Specific Integrated Circuit (ASIC) and a respective Capacitive Micromachined Ultrasonic Transducer (CMUT) which is attached to an upper portion of the corresponding ASIC.

Each of the n first tiles and each of the m second tiles may be disposed such that one side of each respective ASIC and one side of the corresponding CMUT may be disposed collinearly.

Each of the m second tiles may further include an oscillation absorbing material on a side of at least one of the respective ASIC and the corresponding CMUT.

The ultrasonic probe apparatus may include a substrate which includes a jig in which a tile area within which the m second tiles are to be disposed may be patterned along the virtual line, and connected to each of the m second tiles by using a wire.

The virtual line may be provided in a form of at least one of a closed curve and a plurality of straight lines having a single point of contact.

In another general aspect, there is provided a method for manufacturing an ultrasonic probe apparatus, the method including providing a substrate which includes a jig in which a tile area within which tiles are to be disposed may be patterned, disposing, in the jig, n first tiles which transmit an ultrasonic beam toward a target object, and disposing, in the jig and along a virtual line that is provided in a predetermined form, m second tiles which receive an ultrasonic beam that is reflected from the target object. In particular, each of n and m denotes a natural number.

Other features and aspects will be apparent from the following detailed description, the drawings, and the claims.

Figure 1:
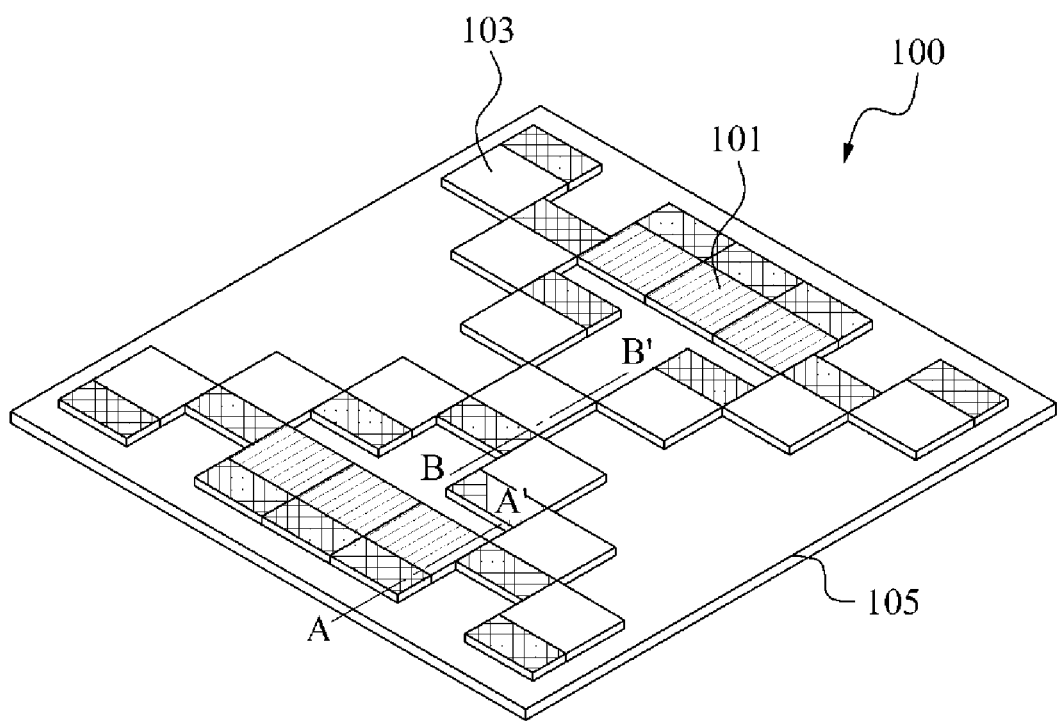
FIG. 1 is a perspective view which illustrates a structure of an ultrasonic probe apparatus, according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing steps and/or operations described is an example; however, the sequence of and/or operations is not limited to that set forth herein and may be changed as is known in the art, with the exception of steps and/or operations necessarily occurring in a particular order.

In addition, respective descriptions of well-known functions and constructions may be omitted for increased clarity and conciseness.

FIG. 1 illustrates a structure of an ultrasonic probe apparatus 100, according to an exemplary embodiment.

Referring to FIG. 1, the ultrasonic probe apparatus 100 includes at least one first tile 101, at least one second tile 103, and a substrate 105.

In the ultrasonic probe apparatus 100, n first tiles 101 may be provided, and the n first tiles 101 may transmit an ultrasonic beam toward a target object. In particular, n denotes a natural number. The n first tiles 101 may be disposed on the substrate 105, in a tile area of a jig (not shown) that is patterned with respect to the n first tiles 101.

More particularly, the n first tiles 101 may include a plurality of respective channels through which the ultrasonic beam may be transmitted. The n first tiles 101 may be disposed such that a gap among respective adjacent pairs of the n first tiles 101 may be maintained to be less than a predetermined value, for example, tens of micrometers (µm).

The n first tiles 101 may be disposed, for example, collinearly. However, the disposition of the n first tiles 101 is not to be limited thereto.

As an example, m second tiles 103 may be provided, and the m second tiles 103 may be disposed along a virtual line that is provided in a predetermined form. In particular, m denotes a natural number. The m second tiles 130 may obtain image data of the target object, by receiving an ultrasonic beam that may be reflected from the target object. In an exemplary embodiment, the virtual line may be provided in a form of a closed curve, for example a circular form, a rhombic form, and the like, or in a form of a plurality of straight lines having a single point of contact, for example, an X-shaped form.

Accordingly, the ultrasonic probe apparatus 100 may arrange the at least one second tile 103 along a standardized virtual line for feedback processing of an ultrasonic beam to be performed. When compared to a conventional model in which a plurality of tiles are disposed to disperse on a substrate, the ultrasonic probe apparatus 100 may enable such feedback processing of an ultrasonic beam sufficiently through use of a fewer number of tiles, and also promote an increase in a processing rate.

In addition, the ultrasonic probe apparatus 100 may arrange tiles along a virtual line, thereby reducing a number of tiles and achieving a reduction of maintenance costs and heat to be expended, due to a fewer number of tiles being used when compared to the conventional model.

For example, the ultrasonic probe apparatus 100 may dispose receive-only Capacitive Micromachined Ultrasonic Transducer (CMUT) tiles to be tiled in an X shape, and dispose send-only CMUT tiles in a remaining space, thereby enabling a high-density reception signal with respect to a receive-only CMUT tile disposed in a central portion to be smoothly linked to an analog board. In addition, the send-only CMUT tiles in the remaining space may have a fewer number of channels and a low density of transmission signals per channel and thus, may be disposed more readily in a space.

As an example, when the virtual line is set in an X shape, in the ultrasonic probe apparatus 100, the at least one second tile 103 may be arranged along a line connecting two nonadjacent vertices on the substrate 105, whereby a number of tiles may be reduced remarkably, when compared to the conventional model that arranges tiles to disperse throughout the substrate 105.

For example, the ultrasonic probe apparatus 100 may arrange twelve second tiles 103 on a substrate with room for 6×6 tiles, thereby reducing a number of tiles corresponding to twenty-four while achieving an identical effect of transmission and reception function, when compared to a conventional arrangement of thirty-six tiles.

As another example, when the virtual line is set in a circular shape, in the ultrasonic probe apparatus 100, the at least one second tiles 103 may be arranged along a closed curve of the circular shape, thereby enabling feedback processing of an ultrasonic beam to be performed sufficiently using a relatively fewer number of tiles.

The m second tiles 103 may be positioned, on the substrate 105, within a tile area of a jig (not shown) that is patterned with respect to the m second tiles 103.

More particularly, the m second tiles 103 may include a plurality of respective channels through which the reflected ultrasonic beam may be received. Similar to the n first tiles 101, the m second tiles 103 may be disposed such that a gap among respective adjacent pairs of the m second tiles 103 may be maintained to be less than a predetermined value. In order for a maximum amount of an ultrasonic beam to be received, the gap among respective adjacent pairs of the m second tiles 103 may be set to be preferably narrow, and also to be less than or equal to 100 µm in view of easy implementation, interference between beams, and the like.

For example, in order to maintain a gap between CMUT elements to be less than 500 µm, a minimum gap between adjacent tiles is to be set to 100 µm, in view of a space for a CMUT process. When the gap between the CMUT elements is not maintained to be less than 500 µm, a grating robe and a side lobe may increase.

In this instance, the m second tiles 103 may be disposed such that each of the plurality of channels, included in the m second tiles and associated with the ultrasonic beam, may be disposed on the virtual line.

Because each of the m second tiles 103 may be disposed along the virtual line, the m second tiles 103 may be disposed noncollinearly, and may be disposed at different respective heights. When the plurality of second tiles 103 is arranged at different respective heights along the virtual line, a time difference in feeding back an ultrasonic beam may occur with respect to the plurality of second tiles 103. The ultrasonic probe apparatus 100 may obtain three-dimensional image data of the target object.

When second tiles are arranged at different respective heights, a probe footprint may correspond to, for example, a rectangular form.

Each of the at least one first tile 101 and each of the at least one second tile 103 may include a respective Application Specific Integrated Circuit (ASIC) and a respective CMUT which is attached to an upper portion of the corresponding ASIC. In particular, the respective ASIC and the corresponding CMUT may be bonded to each other directly, rather than being connected through an intermediate material, for example, an interposer, whereby electrical characteristics of each first tile 101 and each second tile 103 may be improved.

Each of the at least one first tile 101 and each of the at least one second tile 103 may be attached such that one side of the respective ASIC and one side of the corresponding CMUT may be disposed collinearly. In particular, a footprint of the respective ASIC may differ from a footprint of the corresponding CMUT. For example, an area of the footprint of the respective ASIC may be greater than an area of the footprint of the corresponding CMUT.

Each of the m second tiles 103 disposed along the virtual line may include an oscillation absorbing material, such as, for example, an epoxy, on at least one side of each of the m second tiles 103, in order to reduce a residual oscillation which occurs in the m second tiles 103. In particular, the second tile 103 may include the oscillation absorbing material which may be disposed to be in contact with a side of at least one of the respective ASIC and the corresponding CMUT, in order to effectively reduce the residual oscillation resulting from a frequency oscillation between the ASIC and the CMUT in the second tile 103.

The substrate 105 may correspond to, for example, a printed circuit board (PCB), and each of the n first tiles 101 and each of the m second tiles 103 may be disposed on an upper portion of the substrate 105. In this instance, the substrate 105 may include the jigs, in which tile areas within which each of the n first tiles 101 and each of the m second tiles 103, respectively, is to be disposed may be patterned. In addition, the substrate 105 may be connected to each of the n first tiles 101 and to each of the m second tiles 103 disposed in the respective jigs by using wires, such as, for example, metallic wiring. In particular, each of the jigs may include a thin metallic plate formed of silicon or by metal etching.

The substrate 105 may include a jig, in which a tile area within which the m second tiles 103 are to be disposed is patterned along the virtual line that is provided in the predetermined form, in order to guide positions of the m second tiles 103 such that the m second tiles 103 may be readily disposed along the virtual line.

A performance of the ultrasonic probe apparatus 100 may be improved by separating a first tile which is used to transmit an ultrasonic beam toward a target object, and by separating a second tile which is used to receive an ultrasonic beam which is reflected from the target object. In particular, the ultrasonic probe apparatus 100 may include a send-only first tile which transmits an ultrasonic beam toward a target object, and a receive-only second tile which receives an ultrasonic beam that may be reflected from the target object, and may improve a transmission output and a receiving sensitivity by using a first tile which is suitable for transmission and a second tile which is suitable for reception, thereby obtaining more accurate image data.

The ultrasonic probe apparatus 100 may receive an ultrasonic beam that may be reflected from a target object by using a plurality of second tiles which are disposed on a substrate having a predetermined size, and which are disposed along a virtual line that is provided in a predetermined form, thereby obtaining image data which has a quality which falls within an allowable range, using a relatively low number of second tiles, and improving a rate of processing the image data. Accordingly, the ultrasonic probe apparatus 100 may reduce not only costs but also an amount of heat generated, in association with the reduction of the number of the second tiles.

Although the ultrasonic probe apparatus 100 may separate the first tile which is used to transmit the ultrasonic beam, and the second tile which is used to receive the reflected ultrasonic beam, the present disclosure is not limited thereto. Instead, the ultrasonic prove apparatus 100 may perform both transmission and reception of ultrasonic beams by using a plurality of tiles disposed along a virtual line that is provided in a predetermined form, thereby obtaining image data.

Figure 2:
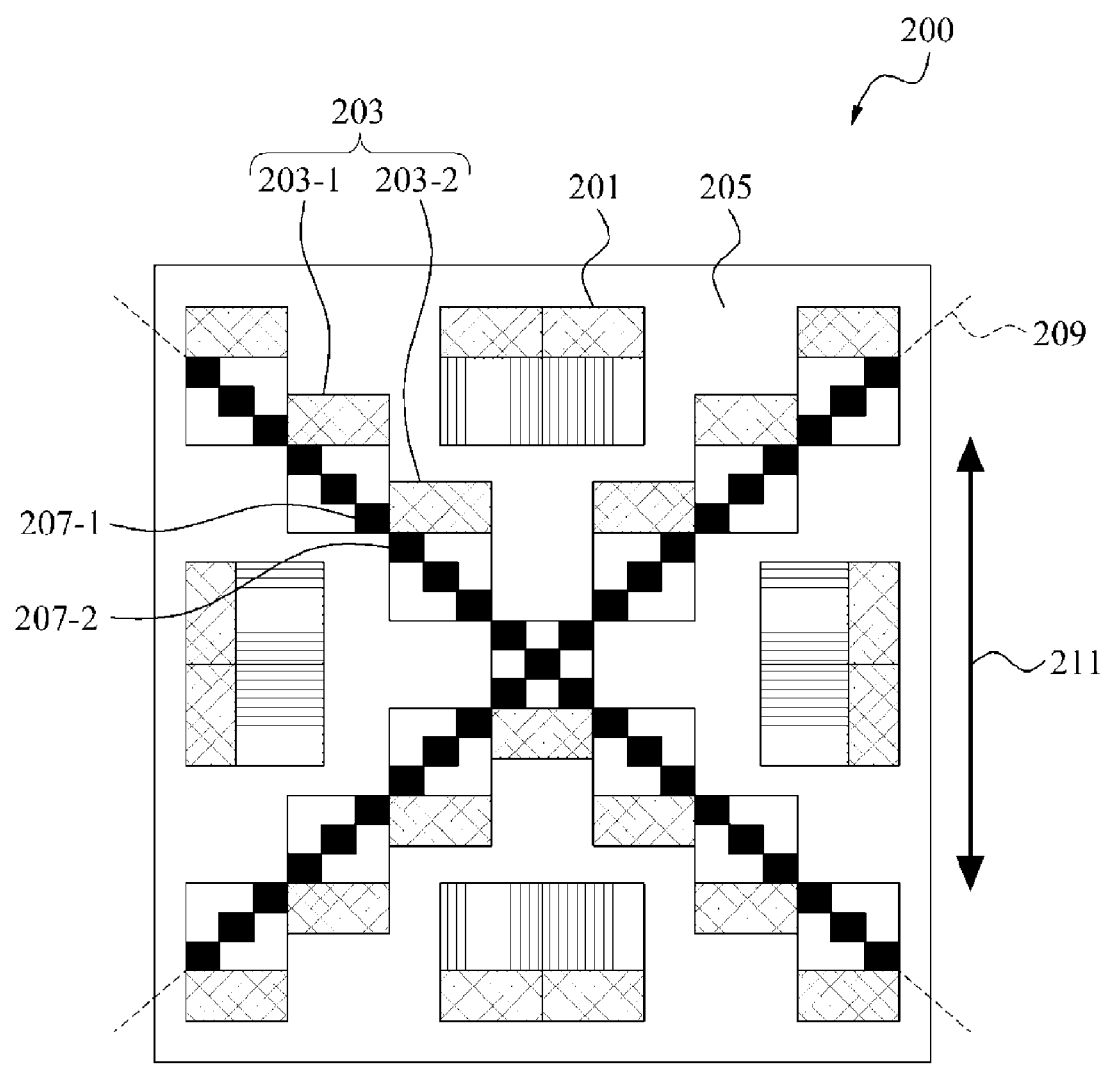
FIG. 2 is a top view which illustrates an ultrasonic probe apparatus, according to an exemplary embodiment.

FIG. 2 illustrates an ultrasonic probe apparatus 200, according to an exemplary embodiment.

Referring to FIG. 2, the ultrasonic probe apparatus 200 includes n first tiles 201 and m second tiles 203. In particular, n and m denote natural numbers. Each of the n first tiles 201 may be disposed on a substrate 205 in order to transmit an ultrasonic beam toward a target object, and each of the m second tiles 203 may be disposed on the substrate 205 along a virtual line that is provided in a predetermined form, in order to receive the ultrasonic beam that may be reflected from the target object.

For example, the ultrasonic probe apparatus 200 may include the m second tiles 203 that may be disposed along a virtual line 209 which is provided in the form of a plurality of straight lines having a single point of contact, such as, for example, in an x-shaped form, as illustrated in FIG. 2.

In an exemplary embodiment, the m second tiles 203 may be disposed such that a gap among respective adjacent pairs of the m second tiles 203 may be maintained to be less than a predetermined value, for example, tens of µm. In particular, each of the m second tiles may include a respective channel which is associated with the ultrasonic beam, and the m second tiles 203 may be disposed such that each respective channel may be arranged on the virtual line 209, which is provided in the form of the plurality of straight lines having the single point of contact. For example, a second tile 203-1 and a second tile 203-2 may be disposed apart from each other by a distance which is less than the predetermined value such that a channel 207-1 which is included in the second tile 203-1 and a channel 207-2 which is included in the second tile 203-2 may be arranged successively along the virtual line 209, which is provided in the form of the plurality of straight lines having the single point of contact, such as, for example, the x-shaped form.

The n first tiles 201 may be disposed in a residual area on the substrate 205, outside of an area in which the m second tiles 203 are disposed along the virtual line 209. For example, the n first tiles 201 may be disposed in an area which lies between the plurality of straight lines.

Because the m second tiles 203 may be disposed along the virtual line 209 which is provided in the predetermined form, the ultrasonic probe apparatus 200 may add tiles above or below the m second tiles 203, thereby expanding channels in an array elevation direction 211.

Figure 3:
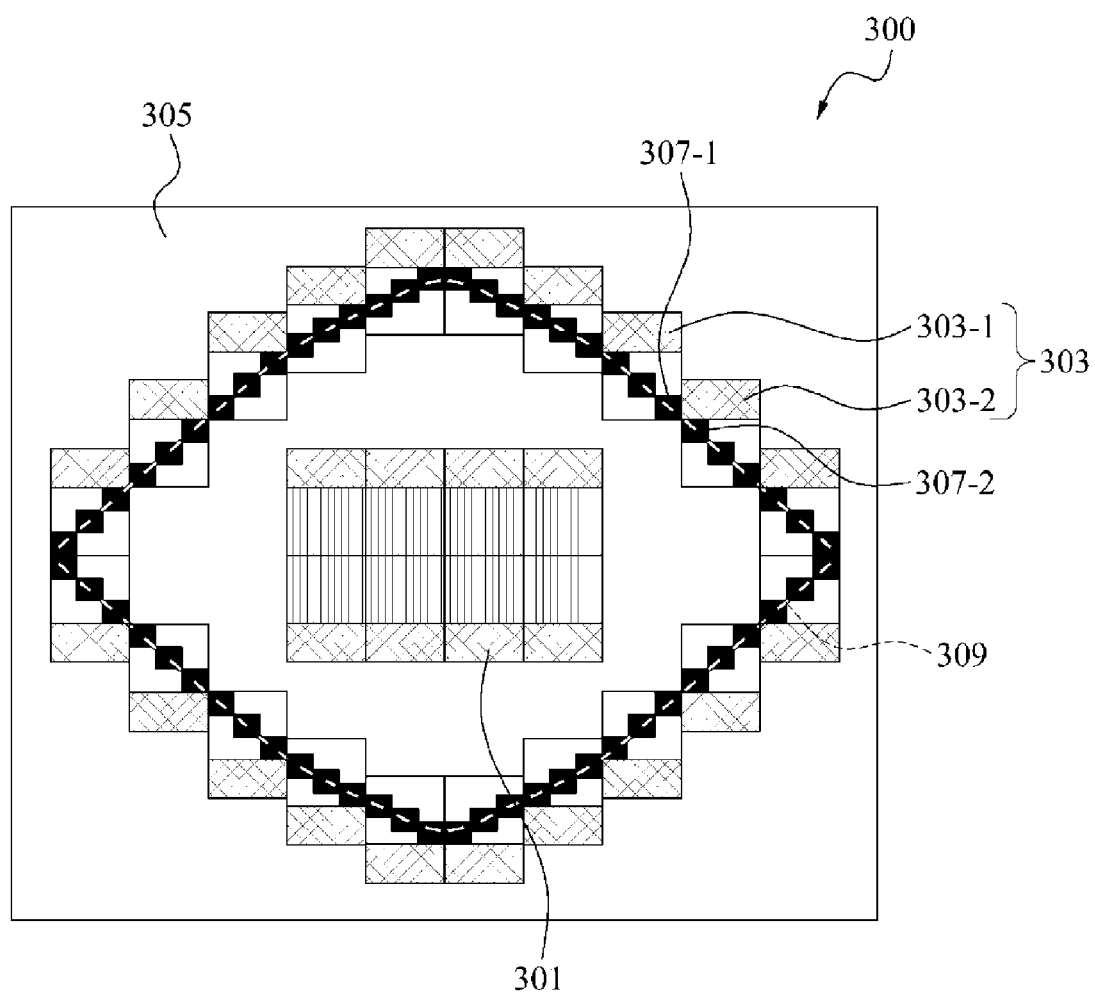
FIG. 3 is a top view which illustrates an ultrasonic probe apparatus, according to another exemplary embodiment.

FIG. 3 illustrates an ultrasonic probe apparatus 300, according to another exemplary embodiment.

Referring to FIG. 3, the ultrasonic probe apparatus 300 includes n first tiles 301 and m second tiles 303. In particular, n and m denote natural numbers. Each of the n first tiles 301 may be disposed on a substrate 305 in order to transmit an ultrasonic beam toward a target object, and each of the m second tiles 303 may be disposed on the substrate 305 along a virtual line that is provided in a predetermined form, in order to receive the ultrasonic beam that may be reflected from the target object.

For example, the ultrasonic probe apparatus 300 may include the m second tiles 303 that may be disposed along a virtual line 309 which is provided in a form of a closed curve, such as, for example, a circular form, a rhombic form, and the like, as illustrated in FIG. 3.

In particular, the m second tiles 303 may be disposed such that a gap among respective adjacent pairs of the m second tiles 303 may be maintained to be less than a predetermined value, for example, tens of µm. In particular, each of the m second tiles 303 may include a respective channel which is associated with the ultrasonic beam, and the m second tiles 303 may be disposed such that each respective channel may be arranged on the virtual line 309 which is provided in the form of the closed curve. For example, a second tile 303-1 and a second tile 303-2 may be disposed apart from each other by a distance which is less than the predetermined value such that a channel 307-1 which is included in the second tile 303-1 and a channel 307-2 which is included in the second tile 303-2 may be arranged successively along the virtual line 309 which is provided in the form of the closed curve, for example, the rhombic form.

Each of the n first tiles 301 may be disposed in a residual area on the substrate 305, outside of an area in which the m second tiles 303 are disposed along the virtual line 309. For example, the n first tiles 301 may be disposed in an internal area of the closed curve, as illustrated in FIG. 3.

Figure 4:
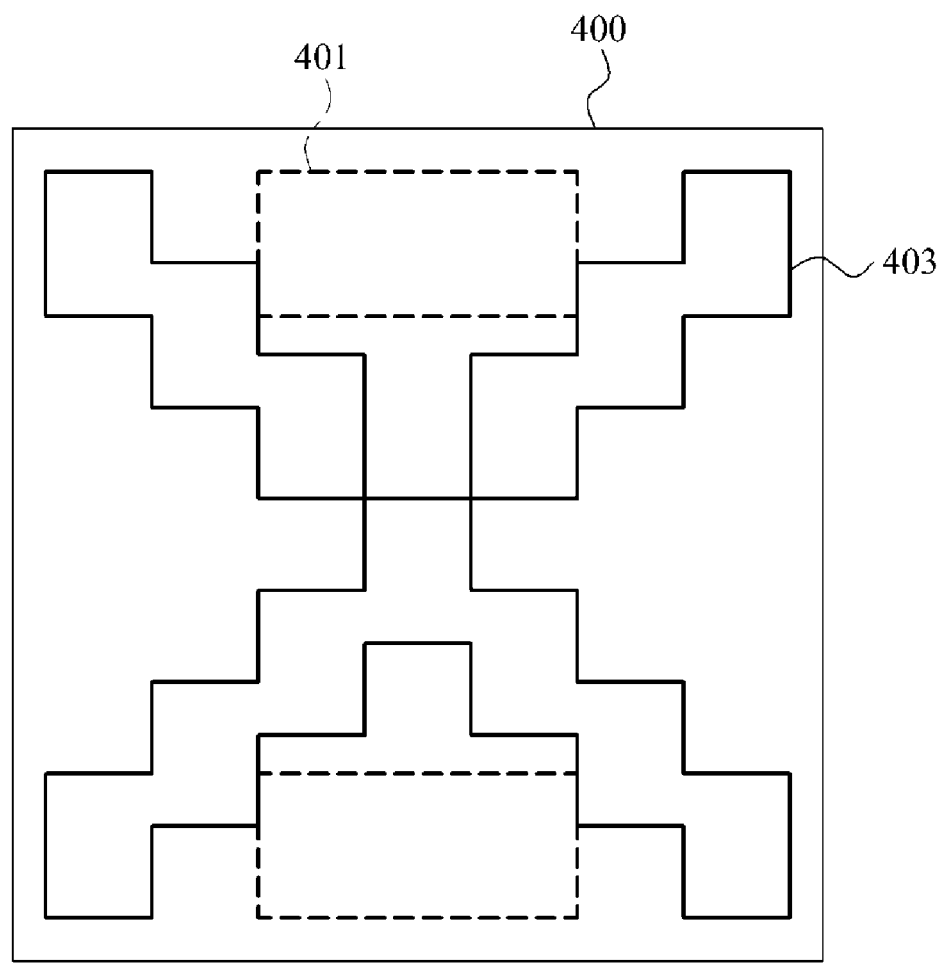
FIG. 4 is a view which illustrates a substrate in an ultrasonic probe apparatus, according to an exemplary embodiment.

FIG. 4 illustrates a substrate 400 in an ultrasonic probe apparatus, according to an exemplary embodiment.

Referring to FIG. 4, the ultrasonic probe apparatus may include the substrate 400 which may be disposed below n first tiles which are used to transmit an ultrasonic beam toward a target object, and below m second tiles which are used to receive the ultrasonic beam that may be reflected from the target object.

In particular, the substrate 400 may correspond to a PCB. The substrate 400 includes a jig 401 in which a tile area within which each of the n first tiles is to be disposed is patterned, and a jig 403 in which a tile area within which each of the m second tiles is to be disposed is patterned. In this instance, the jig 403 may be positioned along a virtual line that is provided in a predetermined form, for example a form of a closed curve, or a form of a plurality of straight lines having a single point of contact, in order to guide positions of the m second tiles such that the m second tiles may be readily disposed along the virtual line.

In particular, each of the jig 401 and the jig 403 may include a thin metallic plate which may be formed, for example, of silicon or by metal etching.

The substrate 400 may be connected to each of the n first tiles which is disposed in the jig 401, and to each of the m second tiles which is disposed in the jig 403, by using wires, such as, for example, metallic wiring.

Figure 5A:
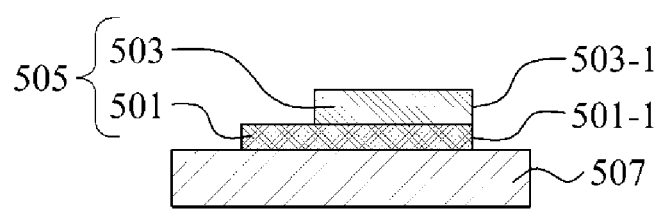
FIGS. 5A and 5B are views which illustrate a first tile in an ultrasonic probe apparatus, according to an exemplary embodiment.
Figure 5B:
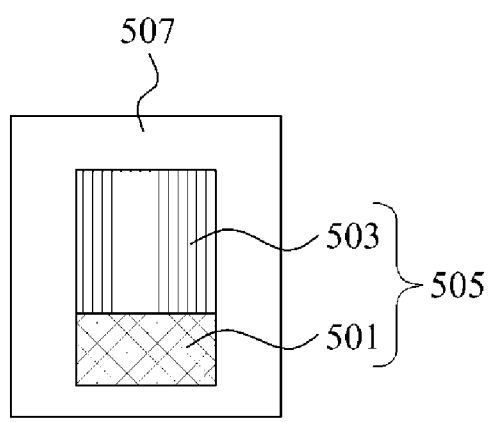

FIGS. 5A and 5B illustrate a first tile in an ultrasonic probe apparatus, according to an exemplary embodiment. In particular, FIG. 5A illustrates a cross-sectional view of the first tile 101 of FIG. 1, which is cut along a line A-A', and FIG. 5B illustrates a top view of the first tile 101.

Referring to FIGS. 5A and 5B, a first tile 505, which is disposed on a substrate 507 in order to transmit an ultrasonic beam, includes an ASIC 501 and a CMUT 503. In this instance, the ASIC 501 and the CMUT 503 may be laminated sequentially. In particular, the first tile 505 includes the ASIC 501 and the CMUT 503 which is attached to an upper portion of the ASIC 501.

Because the ASIC 501 and the CMUT 503 may be bonded to each other directly, without using an intermediate material, such as, for example, an interposer, between the ASIC 501 and the CMUT 503, the first tile 505 may prevent degradation of an electrical characteristic of the first tile 505, thereby preventing, for example, a crosstalk, a parasitic capacitance, and the like. In this instance, the ASIC 501 and the CMUT 503 may be attached to each other, for example, by using flip chip bonding technology.

The first tile 505 may be attached such that one side 501-1 of the ASIC 501 and one side 503-1 of the CMUT 503 may be disposed collinearly. In particular, the first tile 505 may be attached such that the side 503-1 of the CMUT 503 may be disposed directly above the side 501-1 of the ASIC 501.

In an exemplary embodiment, a size of the ASIC 501 may differ from a size of the CMUT 503. For example, the size of the ASIC 501 may be greater than the size of the CMUT 503.

Figure 6A:
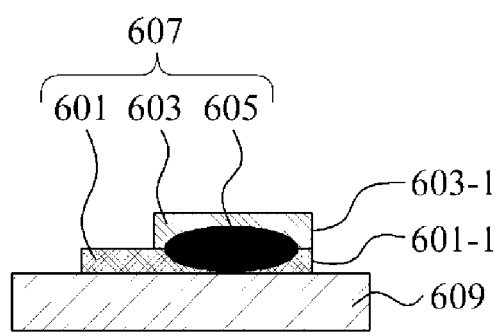
FIGS. 6A and 6B are views which illustrate a second tile in an ultrasonic probe apparatus, according to an exemplary embodiment.
Figure 6B:
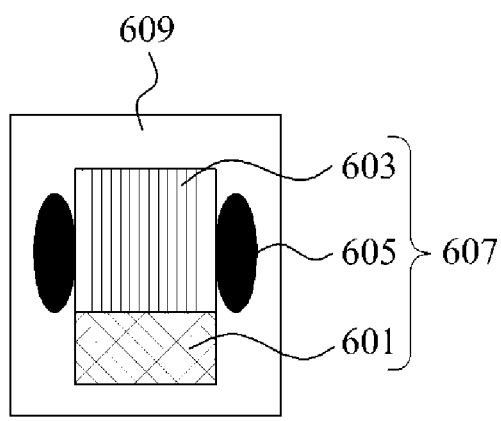

FIGS. 6A and 6B illustrate a second tile in an ultrasonic probe apparatus, according to an exemplary embodiment. In particular, FIG. 6A illustrates a cross-sectional view of the second tile 103 of FIG. 1, which is cut along a line B-B', and FIG. 6B illustrates a top view of the second tile 103.

Referring to FIGS. 6A and 6B, a second tile 607, which is disposed on a substrate 609 in order to receive an ultrasonic beam, includes at least one of an ASIC 601, a CMUT 603, and an oscillation absorbing material 605. In this instance, the ASIC 601 and the CMUT 603 may be laminated sequentially. In particular, the second tile 607 includes the ASIC 601 and the CMUT 603 which is attached to an upper portion of the ASIC 601.

Because the ASIC 601 and the CMUT 603 may be bonded to each other directly, without using an intermediate material, such as, for example, an interposer, between the ASIC 601 and the CMUT 603, the second tile 607 may prevent degradation of an electrical characteristic of the second tile 607, thereby preventing, for example, a crosstalk, a parasitic capacitance, and the like. In this instance, the ASIC 601 and the CMUT 603 may be attached to each other, for example, by using flip chip bonding technology.

The second tile 607 may be attached such that one side 601-1 of the ASIC 601 and one side 603-1 of the CMUT 603 may be disposed collinearly. In particular, the second tile 607 may be attached such that the side 603-1 of the CMUT 603 may be disposed directly above the side 601-1 of the ASIC 601.

In an exemplary embodiment, a size of the ASIC 601 may differ from a size of the CMUT 603. For example, the size of the ASIC 601 may be greater than the size of the CMUT 603.

In addition, the second tile 607 may include the oscillation absorbing material 605 on at least one side of the second tile 607 in order to reduce a residual oscillation which occurs in the second tile 607.

In particular, the oscillation absorbing material 605 may be disposed on a side of at least one of the ASIC 601 and the CMUT 603. More particularly, the oscillation absorbing material 605 may be disposed to be in contact with at least one of the ASIC 601 and the CMUT 603 in order to absorb the residual oscillation effectively.

The second tile 607 is not limited to receiving of the ultrasonic beam, and may transmit an ultrasonic beam.

Figure 7:
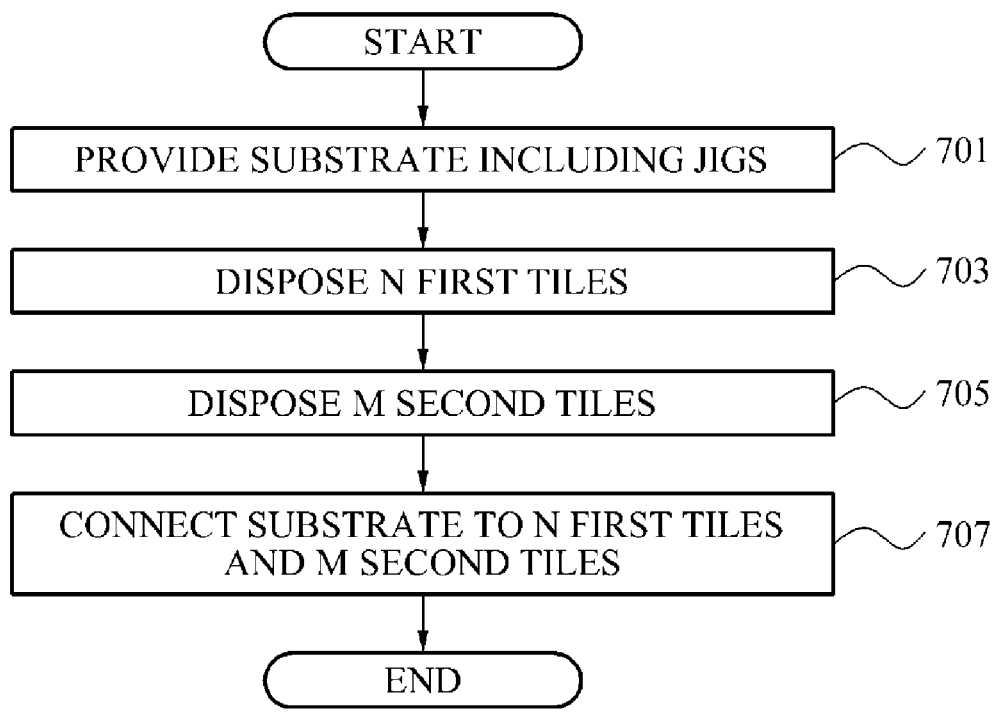
FIG. 7 is a flowchart which illustrates a method for manufacturing an ultrasonic probe apparatus, according to an exemplary embodiment.

FIG. 7 illustrates a method for manufacturing an ultrasonic probe apparatus, according to an exemplary embodiment.

Referring to FIG. 7, in operation 701, a substrate including jigs in which tile areas within which tiles are to be disposed are respectively patterned is provided.

In operation 703, n first tiles which transmit an ultrasonic beam toward a target object are disposed in one jig on the substrate. In particular, n denotes a natural number.

In an exemplary embodiment, the n first tiles may be disposed within the tile area of the jig which is patterned with respect to the n first tiles.

Each of the n first tiles may include a respective channel through which a respective ultrasonic beam may be transmitted. The n first tiles may be disposed such that a gap among respective adjacent pairs of the n first tiles may be maintained to be less than a predetermined value, for example, tens of μm.

A first tile may include a respective ASIC and a respective CMUT which is attached to an upper portion of the corresponding ASIC.

In this instance, the first tile may be attached such that one side of the respective ASIC and one side of the corresponding CMUT may be disposed collinearly. In particular, a footprint of the respective ASIC may differ from a footprint of the corresponding CMUT. For example, the area of the footprint of the respective ASIC may be greater than area of the footprint of the corresponding CMUT. Because the footprint of the respective ASIC may differ from the footprint of the corresponding CMUT, another side of the respective ASIC and another side of the corresponding CMUT may not be disposed collinearly when the first tile is attached such that the one side of the respective ASIC and the one side of the corresponding CMUT may be disposed collinearly.

In operation 705, m second tiles which receive the ultrasonic beam that may be reflected from the target object are disposed in another jig on the substrate, along a virtual line that is provided in a predetermined form. In particular, m denotes a natural number.

As an example, the m second tiles may be disposed within the tile area of the other jig which is patterned along a virtual line with respect to the m second tiles. In particular, the m second tiles may be disposed within the tile area of the other jig which is patterned along the virtual line, and may disposed on the substrate in a form of a closed curve, or in a form of a plurality of straight lines having a single point of contact.

Each of the m second tiles may include a respective channel through which the ultrasonic beam may be received. Similar to the n first tiles, the m second tiles may be disposed such that a gap among respective adjacent pairs of the m second tiles may be maintained to be less than a predetermined value, for example, tens of $\mu$m. In this instance, the m second tiles may be disposed on the substrate such that each of the plurality of respective channels, which are included in the m second tiles and which are associated with the ultrasonic beam, may be disposed on the virtual line.

Similar to the first tile, a second tile may include a respective ASIC and a respective CMUT which is attached to an upper portion of the corresponding ASIC.

In this instance, the second tile may be attached such that one side of the respective ASIC and one side of the corresponding CMUT may be disposed collinearly. In particular, a footprint of the respective ASIC may differ from a footprint of the corresponding CMUT. For example, an area of the footprint of the respective ASIC may be greater than an area of the footprint of the corresponding CMUT. Because the footprint of the respective ASIC may differ from the footprint of the corresponding CMUT, another side of the respective ASIC and another side of the corresponding CMUT may not be disposed collinearly when the second tile is attached such that the one side of the respective ASIC and the one side of the corresponding CMUT may be disposed collinearly.

In addition, the second tile may include an oscillation absorbing material, such as, for example, an epoxy, on a side of at least one of the respective ASIC and the corresponding CMUT in order to reduce a residual oscillation which occurs in the second tile.

In operation 707, the substrate is connected, by using wires, to each of the n first tiles and to each of the m second tiles which are respectively disposed in the jigs on the substrate.

The units described herein may be implemented using hardware components, software components, or a combination thereof. For example, a processing device may be implemented by using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave which is capable of providing instructions or data to or being interpreted by the processing device. The software also may be distributed over network coupled computer systems so that the software is stored and executed in a distributed fashion. In particular, the software and data may be stored by one or more transitory and/or non-transitory computer readable recording mediums.

The computer readable recording medium may include any data storage device that can store data which can be thereafter read by a computer system or processing device. Examples of the non-transitory computer readable recording medium include read-only memory (ROM), random-access memory (RAM), compact disk-ROMs (CD-ROMs), magnetic tapes, floppy disks, and optical data storage devices. In addition, functional programs, codes, and code segments for accomplishing the exemplary embodiments disclosed herein can be easily construed by programmers skilled in the art to which the exemplary embodiments pertain based on and using the flow diagrams and block diagrams of the figures and their corresponding descriptions as provided herein.

According to exemplary embodiments, an ultrasonic probe apparatus may include a send-only first tile which transmits an ultrasonic beam toward a target object, and a receive-only second tile which receives an ultrasonic beam which is reflected from the target object, and may improve a transmission output and a receiving sensitivity by using a first tile which is suitable for transmission and a second tile which is suitable for reception.

According to exemplary embodiments, an ultrasonic probe apparatus may receive an ultrasonic beam that may be reflected from a target object, by using a plurality of second tiles which are disposed on a substrate having a predetermined size, along a virtual line that is provided in a predetermined form, thereby obtaining image data which has a quality which falls within an allowable range, using a relatively low number of second tiles, and improving a rate of processing the image data.

According to exemplary embodiments, an ultrasonic probe apparatus may include a plurality of second tiles which are respectively disposed along a virtual line that is provided in a predetermined form, and may include additional tiles which are disposed above or below the plurality of second tiles with respect to the virtual line, thereby expanding channels in an array elevation direction.

According to exemplary embodiments, an ultrasonic probe apparatus may exhibit improved electrical characteristics of a first tile and a second tile by arranging the first tile and the second tile such that they are bonded to each other directly, without using an intermediate material, such as, for example, an interposer, between an ASIC and a CMUT.

According to exemplary embodiments, an ultrasonic probe apparatus may include an oscillation absorbing material, such as, for example, an epoxy, on at least one side of a second tile in order to reduce a residual oscillation which occurs in the second tile.

A number of exemplary embodiments have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An ultrasonic probe apparatus, comprising:
    n first tiles which are disposed on a substrate and which transmit an ultrasonic beam toward a target object; and
    m second tiles, which are disposed along a virtual line that is provided in a predetermined form with one of a closed curve and a plurality of straight lines having a single point of contact, and which receive an ultrasonic beam that is reflected from the target object,
    wherein each of n and m denotes a natural number, and
    wherein at least one second tile from among the m second tiles is disposed noncollinearly at a different height than other second tiles with respect to the substrate, such that a top surface of the at least one second tile resides in a first plane that is different from and parallel to a second plane within which top surfaces of other second tiles reside.

2. The apparatus of claim 1, wherein each of the m second tiles comprises a respective channel which is associated with the ultrasonic beam, and wherein each of the m second tiles is disposed such that each respective channel is disposed on the virtual line.

3. The apparatus of claim 1, wherein each of the n first tiles and each of the m second tiles is disposed such that each of a first gap among respective adjacent pairs of the n first tiles and a second gap among respective adjacent pairs of the m second tiles is maintained to be less than a predetermined value.

4. The apparatus of claim 1, wherein each of the n first tiles and each of the m second tiles comprises a respective Application Specific Integrated Circuit (ASIC) and a respective Capacitive Micromachined Ultrasonic Transducer (CMUT) which is attached to an upper portion of the corresponding ASIC.

5. The apparatus of claim 4, wherein each of the n first tiles and each of the m second tiles is disposed such that one side of each respective ASIC and one side of the corresponding CMUT are disposed collinearly.

6. The apparatus of claim 4, wherein each of the m second tiles further comprises:
    an oscillation absorbing material on a side of at least one of the respective ASIC and the corresponding CMUT.

7. The apparatus of claim 1, further comprising:
    a substrate which comprises a jig in which a tile area within which the m second tiles are to be disposed is patterned along the virtual line, and connected to each of the m second tiles by using a wire.

8. A method for manufacturing an ultrasonic probe apparatus, the method comprising:
    providing a substrate which comprises a jig in which a tile area within which tiles are to be disposed is patterned;
    disposing, in the jig, n first tiles which transmit an ultrasonic beam toward a target object; and
    disposing, in the jig and along a virtual line that is provided in a predetermined form with one of a closed curve and a plurality of straight lines having a single point of contact, m second tiles which receive an ultrasonic beam that is reflected from the target object,
    wherein each of n and m denotes a natural number, and
    wherein at least one second tile from among the m second tiles is disposed noncollinearly at a different height than other second tiles with respect to the substrate, such that a top surface of the at least one second tile resides in a first plane that is different from and parallel to a second plane within which top surfaces of other second tiles reside.

9. The method of claim 8, wherein each of the m second tiles comprises a respective channel which is associated with the ultrasonic beam, and wherein the disposing the m second tiles comprises disposing each of the m second tiles such that each respective channel is disposed on the virtual line.

10. The method of claim 8, further comprising:
    disposing each of the n first tiles and each of the m second tiles such that each of a first gap among respective adjacent pairs of the n first tiles and a second gap among respective adjacent pairs of the m second tiles is maintained to be less than a predetermined value.

11. The method of claim 8, wherein each of the n first tiles comprises a respective Application Specific Integrated Circuit (ASIC) and a respective Capacitive Micromachined Ultrasonic Transducer (CMUT) which is attached to an upper portion of the corresponding ASIC.

12. The method of claim 11, wherein each of the n first tiles is disposed such that one side of each respective ASIC and one side of the corresponding CMUT are disposed collinearly.

13. The method of claim 8, wherein each of the m second tiles comprises at least one of a respective ASIC, a respective CMUT which is attached to an upper portion of the corresponding ASIC, and an oscillation absorbing material which is disposed on a side of at least one of the respective ASIC and the corresponding CMUT.

14. The method of claim 8, further comprising:
    connecting the substrate to each of the n first tiles and to each of the m second tiles that are disposed in the jig by using a wire.

* * * * *